United States Patent
Ito et al.

(10) Patent No.: US 12,344,691 B2
(45) Date of Patent: Jul. 1, 2025

(54) RESIN COMPOSITION FOR STEREOLITHOGRAPHY

(71) Applicant: KURARAY NORITAKE DENTAL INC., Kurashiki (JP)

(72) Inventors: Misaki Ito, Niigata (JP); Kenji Suzuki, Niigata (JP)

(73) Assignee: KURARAY NORITAKE DENTAL INC., Kurashiki (JP)

(*) Notice: Subject to any disclaimer, the term of this patent is extended or adjusted under 35 U.S.C. 154(b) by 780 days.

(21) Appl. No.: 17/617,160

(22) PCT Filed: Jun. 5, 2020

(86) PCT No.: PCT/JP2020/022438
§ 371 (c)(1),
(2) Date: Dec. 7, 2021

(87) PCT Pub. No.: WO2020/246610
PCT Pub. Date: Dec. 10, 2020

(65) Prior Publication Data
US 2022/0259361 A1 Aug. 18, 2022

(30) Foreign Application Priority Data
Jun. 7, 2019 (JP) .................................. 2019-107405

(51) Int. Cl.
| | |
|---|---|
| A61C 7/08 | (2006.01) |
| A61C 13/01 | (2006.01) |
| A61K 6/889 | (2020.01) |
| A61K 6/893 | (2020.01) |
| B33Y 70/00 | (2020.01) |
| C08F 290/06 | (2006.01) |
| B29C 64/124 | (2017.01) |
| B29K 105/00 | (2006.01) |
| B33Y 10/00 | (2015.01) |

(52) U.S. Cl.
CPC ............ *C08F 290/061* (2013.01); *A61C 7/08* (2013.01); *A61C 13/01* (2013.01); *A61K 6/889* (2020.01); *A61K 6/893* (2020.01); *B33Y 70/00* (2014.12); *A61C 2201/00* (2013.01); *B29C 64/124* (2017.08); *B29K 2105/0002* (2013.01); *B33Y 10/00* (2014.12)

(58) Field of Classification Search
None
See application file for complete search history.

(56) References Cited

U.S. PATENT DOCUMENTS

| | | | | |
|---|---|---|---|---|
| 7,579,066 | B2 * | 8/2009 | Nozawa | C07C 275/24 |
| | | | | 522/74 |
| 8,242,202 | B2 * | 8/2012 | Yamaguchi | C09D 175/16 |
| | | | | 524/556 |
| 8,399,569 | B2 * | 3/2013 | Murofushi | C08G 18/3206 |
| | | | | 525/291 |
| 9,237,990 | B2 * | 1/2016 | Abuelyaman | C08L 33/08 |
| 10,611,964 | B2 * | 4/2020 | Kobayashi | C07C 43/215 |
| 11,045,834 | B2 * | 6/2021 | Taguchi | B05D 7/24 |
| 11,554,539 | B2 * | 1/2023 | Provin | G03F 7/2012 |
| 11,780,947 | B2 * | 10/2023 | Sakamaki | C08F 20/30 |
| | | | | 433/202.1 |
| 11,992,539 | B2 * | 5/2024 | Homnick | A61K 6/71 |
| 2013/0090031 | A1 * | 4/2013 | Sismondi | C03C 25/323 |
| | | | | 442/178 |
| 2017/0233594 | A1 | 8/2017 | Yoda et al. | |
| 2018/0079923 | A1 | 3/2018 | Umebayashi | |
| 2021/0038353 | A1 | 2/2021 | Sakamaki | |
| 2022/0242991 | A1 * | 8/2022 | Klun | C08G 18/8038 |

FOREIGN PATENT DOCUMENTS

| | | | |
|---|---|---|---|
| EP | 2 960 718 A1 | 12/2015 | |
| EP | 3 960 123 A1 | 3/2022 | |
| JP | 56-144478 A | 11/1981 | |
| JP | 60-247515 A | 12/1985 | |
| JP | 2000-159621 A | 6/2000 | |
| JP | 2015-10169 A | 1/2015 | |
| JP | 2016-20474 A | 2/2016 | |
| JP | 2016-102208 A | 6/2016 | |
| JP | 2017-141381 A | 8/2017 | |
| WO | WO-2013022065 A1 * | 2/2013 | ............ C08F 20/30 |
| WO | WO 2016/199611 A1 | 12/2016 | |
| WO | WO-2018143303 A1 * | 8/2018 | ........... B29C 64/112 |
| WO | WO 2018/181832 A1 | 10/2018 | |
| WO | WO-2019021453 A1 * | 1/2019 | ........... B29C 64/124 |
| WO | WO 2019/189566 A1 | 10/2019 | |

OTHER PUBLICATIONS

International Search Report issued on Aug. 18, 2020 in PCT/JP2020/022438 filed Jun. 5, 2020, 3 pages.
Extended European Search Report issued May 31, 2023 in European Patent Application No. 20819114.8, 11 pages.

* cited by examiner

*Primary Examiner* — Sanza L. McClendon
(74) *Attorney, Agent, or Firm* — Oblon, McClelland, Maier & Neustadt, L.L.P.

(57) ABSTRACT

A resin composition for stereolithography may emit a weak odor, enable easy fabrication of an object, and may be made into a cured product having desirable toughness and water resistance when used for stereolithographical fabrication. A resin composition for stereolithography may include: an α,β-unsaturated double bond group-containing compound (A) having a homopolymer glass transition temperature (Tg) of 40° C. or more, having a plurality of independent aromatic rings, and having no urethane bond; an α,β-unsaturated double bond group-containing compound (B) having a homopolymer glass transition temperature (Tg) of less than 40° C., having a ring structure, and having a normal boiling point of 250° C. or more; and a photopolymerization initiator (C).

24 Claims, No Drawings

RESIN COMPOSITION FOR STEREOLITHOGRAPHY

CROSS-REFERENCE TO RELATED APPLICATIONS

The present application is the national stage of international application PCT/JP2020/022438, filed on Jun. 5, 2020, and claims the benefit of the filing date of Japanese Appl. No. 2019-107405, filed on Jun. 7, 2019.

TECHNICAL FIELD

The present invention relates to a resin composition for stereolithography. Specifically, according to the present invention, a three-dimensional object emitting a weak odor, easily fabricated, and having desirable toughness and water resistance can be obtained by stereolithographical fabrication. The resin composition for stereolithography of the present invention is particularly suited for dental mouthpieces and denture base materials.

BACKGROUND ART

Patent Literature 1 discloses a stereolithographic modeling technique, a method that produces a three-dimensional object through repeated exposure of controlled, necessary amounts of light energy to a liquid photocurable resin to cure the resin layer-by-layer as it is supplied onto the previously cured layer. Patent Literature 2 proposes a basic method for practical application of this technique, and, since its proposal, many other stereolithographic modeling techniques have been proposed.

Vat stereolithography is a technique commonly used for optical fabrication of a three-dimensional object. In this technique, a computer-controlled ultraviolet laser is selectively applied to draw the desired pattern on the surface of a liquid photocurable resin composition placed in a vat. By being cured, the resin forms a layer of a predetermined thickness, and another cured layer is continuously formed on the cured layer by applying an ultraviolet laser to the liquid photocurable resin composition supplied onto the previously cured layer in an amount necessary to form a single layer. The layering process is repeated to produce a three-dimensional object of the desired shape. This technique has attracted great interest because it enables easy and precision production of the desired three-dimensional object in a relatively short time period, even when the product has a very complex shape.

Three-dimensional objects produced by stereolithography are used in an increasingly wider range of applications, from simple concept models to more complex models such as test models and prototypes. This has created a demand for higher shape accuracy in these three-dimensional objects. In addition to satisfying such properties, these products are also required to have properties that are suited for their intended use. The field of dental materials is thought to greatly benefit from stereolithography because dental mouthpieces and denture bases require shapes that vary from patient to patient, aside from being complex in shape.

Dental mouthpieces are dental aligners attached to teeth for correction of teeth alignment, dental splints attached for correction of jaw position, those worn during sleep for treatment of sleep apnea, those attached to the oral cavity to lessen an external injury caused by application of a large external force to the teeth and the jaw bone and protect the stomatognathic system and the brain in contact sport games. In orthodontics, the use of dental mouthpieces has gained wide popularity over the last years because of aesthetics or detachability. Dental mouthpieces are also increasingly being used as appliances for the treatment of sleep apnea, which has attracted medical interest amongst other sleep disorders.

Denture base materials are materials used for the gum as a part of a denture attached to replace missing teeth. The demand for dentures has rapidly increased in recent years because of increasing ageing populations.

Common requirements for dental mouthpieces and denture base materials include toughness and water resistance. A loss of toughness leads to discomfort, or causes the impact of external forces and biting to directly transmit to the jawbones. Being prone to fractures is also problematic because it necessitates frequent replacement. A loss of water resistance makes these appliances practically useless as it causes reduction of mechanical strength, inability to deliver orthodontic forces or absorb shock, and weak fracture resistance.

Another consideration is that fabrication of dental mouthpieces, denture base materials, and appliances for treatment of sleep apnea typically requires taking an impression of the oral cavity. However, it has been pointed out that the procedure brings discomfort for patients and is a burden for them and that the procedure requires high technical skills. Recent advances in digital technology has led to approaches that make use of an intraoral optical scan for taking an oral impression, and there have been attempts to apply stereolithographic modeling techniques for molding. For fabrication, photocurable resin compositions are used. As a rule, resin compositions that develop flexibility and water resistance are usually high in low-polarity monomers and low in curability, and cured products of such resin compositions tend to have poor mechanical strength. Particularly, in stereolithographic modeling, light is applied for only brief time periods, and the resin composition is exposed to oxygen as it is fabricated into an object layer-by-layer. This often leads to defects, notably insufficient curing. Indeed, it has been difficult to satisfy mechanical strength, toughness, and water resistance at the same time. Resin compositions are also required to have adequate viscosity for fabrication. Use of low-molecular-weight monomers to achieve low-viscosity resin compositions, however, tends to produce odors. On the other hand, many of monomers that develop mechanical strength have high viscosity, which decreases fabricability of the resulting resin compositions. Therefore, it is difficult in general to obtain a resin composition for modeling that has a low viscosity and from which a cured product having good properties such as high toughness and water resistance can be made.

Against this background, various techniques are proposed that are intended to achieve desirable shape accuracy, produce a cured product having desirable mechanical strength and swelling resistance, and enable stereolithographic modeling. For example, Patent Literature 3 proposes a resin composition for stereolithographic modeling including at least, as essential components, an oligomer having one or more $\alpha,\beta$-unsaturated double bond groups and an $\alpha,\beta$-unsaturated double bond group-containing compound having a tricyclic or higher ring structure.

CITATION LIST

Patent Literature

Patent Literature 1: JP S56(1981)-144478 A
Patent Literature 2: JP S60(1985)-247515 A
Patent Literature 3: JP 2015-010169 A

SUMMARY OF INVENTION

Technical Problem

Patent Literature 3 does not describe anything about water resistance and an odor of the resin composition for stereolithographic modeling, and a monomer having a notable odor is used in examples.

It is accordingly an object of the present invention to provide a resin composition for stereolithography emitting a weak odor, enabling easy fabrication of an object, and made into a cured product having desirable toughness and water resistance when used for stereolithographical fabrication. Another object of the present invention is to provide a resin composition for stereolithography particularly suited for dental mouthpieces and denture base materials.

Solution to Problem

Specifically, the present invention includes the following aspects.

[1] A resin composition for stereolithography, comprising:
an α,β-unsaturated double bond group-containing compound (A) having a homopolymer glass transition temperature (Tg) of 40° C. or more, having a plurality of independent aromatic rings, and having no urethane bond;
an α,β-unsaturated double bond group-containing compound (B) having a homopolymer glass transition temperature (Tg) of less than 40° C., having a ring structure, and having a normal boiling point of 250° C. or more; and
a photopolymerization initiator (C).

[2] The resin composition for stereolithography according to [1], wherein the α,β-unsaturated double bond group-containing compound (A) is a monofunctional compound.

[3] The resin composition for stereolithography according to [1], wherein the α,β-unsaturated double bond group-containing compound (A) is a monofunctional (meth)acrylic acid ester compound (A)-1.

[4] The resin composition for stereolithography according to any one of [1] to [3], wherein the plurality of independent aromatic rings are each a biphenyl skeleton, a diphenylmethyl skeleton, a 2,2-diphenylpropane skeleton, a triphenylmethyl skeleton, a diphenyl ether skeleton, a fluorene skeleton, a carbazole skeleton, or a diphenylamine skeleton.

[5] The resin composition for stereolithography according to any one of [1] to [3], wherein the plurality of independent aromatic rings are each a biphenyl skeleton, a diphenylmethyl skeleton, a 2,2-diphenylpropane skeleton, a triphenylmethyl skeleton, a diphenyl ether skeleton, a fluorene skeleton, or a diphenylamine skeleton.

[6] The resin composition for stereolithography according to any one of [1] to [3], wherein the plurality of independent aromatic rings are each a triphenylmethyl skeleton or a fluorene skeleton.

[7] The resin composition for stereolithography according to any one of [1] to [6], wherein the α,β-unsaturated double bond group-containing compound (A) is at least one selected from the group consisting of triphenylmethyl (meth)acrylate, 9-(meth)acryloyloxyfluorene, and 9-(meth)acryloyloxymethylfluorene.

[8] The resin composition for stereolithography according to any one of [1] to [7], wherein the α,β-unsaturated double bond group-containing compound (B) is a monofunctional compound.

[9] The resin composition for stereolithography according to any one of [1] to [8], wherein the α,β-unsaturated double bond group-containing compound (B) is a monofunctional (meth)acrylic acid ester compound (B)-1.

[10] The resin composition for stereolithography according to any one of [1] to [9], wherein the ring structure is an aromatic ring.

[11] The resin composition for stereolithography according to any one of [1] to [10], wherein the α,β-unsaturated double bond group-containing compound (B) is at least one selected from the group consisting of o-phenoxybenzyl acrylate, m-phenoxybenzyl acrylate, p-phenoxybenzyl acrylate, 2-(o-phenoxyphenyl)ethyl acrylate, 2-(m-phenoxyphenyl)ethyl acrylate, 2-(p-phenoxyphenyl)ethyl acrylate, ethoxylated-o-phenylphenol (meth)acrylate, ethoxylated-m-phenylphenol (meth)acrylate, and ethoxylated-p-phenylphenol (meth)acrylate.

[12] The resin composition for stereolithography according to any one of [1] to [11], further comprising a urethanized (meth)acrylic compound (D) excluding those falling under the α,β-unsaturated double bond group-containing compound (B).

[13] The resin composition for stereolithography according to [12], wherein the urethanized (meth)acrylic compound (D) is a (meth)acrylate having, per molecule, a urethane bond and at least one structure selected from the group consisting of a polyester, a polycarbonate, a polyurethane, a polyether, a poly(conjugated diene), and a hydrogenated poly(conjugated diene).

[14] The resin composition for stereolithography according to [13], wherein the urethanized (meth)acrylic compound (D) is a (meth)acrylate having, per molecule, at least one polyol moiety selected from the group consisting of a polyester, a polycarbonate, a polyurethane, a polyether, a poly(conjugated diene), and a hydrogenated poly(conjugated diene) each having a structure derived from a C4 to C18 aliphatic diol unit (d) having a branched structure.

[15] A dental material comprising a cured product of the resin composition for stereolithography according to any one of [1] to [14].

[16] A dental mouthpiece comprising a cured product of the resin composition for stereolithography according to any one of [1] to [14].

[17] A denture base material comprising a cured product of the resin composition for stereolithography according to any one of [1] to [14].

[18] A material for treatment of a sleep disorder, comprising a cured product of the resin composition for stereolithography according to any one of [1] to [14].

[19] A method for producing a three-dimensional object with the resin composition for stereolithography according to any one of [1] to [14] by stereolithographic modeling.

Advantageous Effects of Invention

The resin composition for stereolithography of the present invention emits a weak odor, enables easy fabrication of an object, and is made into a cured product having desirable toughness and water resistance when used for stereolithographical fabrication. Therefore, the resin composition for stereolithography of the present invention can be used suitably for various dental materials (particularly dental mouthpieces and denture base materials) or various sleep disorder treatment materials (particularly appliances for treatment of sleep apnea).

DESCRIPTION OF EMBODIMENTS

The resin composition for stereolithography of the present invention is a resin composition for stereolithography comprising: an α,β-unsaturated double bond group-containing compound (A) having a homopolymer glass transition temperature (Tg) of 40° C. or more, having a plurality of independent aromatic rings, and having no urethane bond; an α,β-unsaturated double bond group-containing compound (B) having a homopolymer glass transition temperature (Tg) of less than 40° C., having a ring structure, and having a normal boiling point of 250° C. or more; and a photopolymerization initiator (C). In the present specification, the upper limits and lower limits of numeric ranges (for example, ranges of contents of components, ranges of values calculated from components, and numeric ranges of physical properties) can be combined appropriately.

A,B-Unsaturated Double Bond Group-Containing Compound (A) Having a Homopolymer Glass Transition Temperature (Tg) of 40° C. or More, Having a Plurality of Independent Aromatic Rings, and Having No Urethane Bond Because increasing a melting point (Tm) or glass transition temperature (Tg) of a three-dimensional object, the α,β-unsaturated double bond group-containing compound (A) having a homopolymer glass transition temperature (Tg) of 40° C. or more, having a plurality of independent aromatic rings, and having no urethane bond (hereinafter, also referred to simply as "α,β-unsaturated double bond group-containing compound (A)") further improves internal cohesion of a light-irradiated three-dimensional object and enables formation of a three-dimensional object having favorable toughness including strength.

It is important that a homopolymer of the α,β-unsaturated double bond group-containing compound (A) of the present invention have a glass transition temperature (Tg) of 40° C. or more. With a homopolymer glass transition temperature (Tg) of 40° C. or more, a rigid structure is introduced, and therefore a three-dimensional object having favorable strength can be formed. The homopolymer Tg is preferably 60° C. or more, more preferably 80° C. or more, even more preferably 100° C. or more. The upper limit of the homopolymer Tg is not particularly limited, and is preferably 400° C. or less, more preferably 300° C. or less, even more preferably 250° C. or less. In the present invention, the glass transition temperature (Tg) of a compound can be measured by a known method using a viscoelasticity measuring apparatus (rheometer), a differential scanning calorimeter (DSC), or the like. For example, the temperature at which tan δ reaches a peak can be determined as the glass transition temperature (Tg) of the (meth)acrylic compound (A) by dynamic viscoelastic measurement thereof in which a frequency is 10 Hz, a load is 10 N, a displacement is 0.1%, and a torque is 20 μNm using a rotational rheometer ("AR2000" manufactured by TA Instruments Japan Inc.).

It is important for the α,β-unsaturated double bond group-containing compound (A) of the present invention to have the plurality of independent aromatic rings. In the present specification, the term "plurality of independent aromatic rings" excludes fused-ring compounds having a skeleton (such as a naphthalene skeleton, a phenanthrene skeleton, a phenalene skeleton, or an anthracene skeleton) in which two or more aromatic rings are directly bonded to each other. With the plurality of independent aromatic rings, solubility is increased and a rigid structure is introduced, and therefore a three-dimensional object having favorable strength can be formed.

It is important for the α,β-unsaturated double bond group-containing compound (A) of the present invention not to have a urethane bond. A urethane bond in the α,β-unsaturated double bond group-containing compound (A) would increase the viscosity of the resulting resin composition for modeling and decrease fabricability thereof.

In the present specification, the term "α,β-unsaturated double bond group" represents a polymerizable group such as a (meth)acryloyl group, a vinyl group, or a styrene group. In a suitable embodiment, the α,β-unsaturated double bond group is a (meth)acryloyl group. In view of obtaining a cured product having desirable toughness, the α,β-unsaturated double bond group-containing compound (A) of the present invention is preferably a monofunctional compound, more preferably a monofunctional (meth)acrylic acid ester compound (A)-1. In the present specification, the term "monofunctional" is used to mean that the number of above polymerizable groups is one. In the present specification, the term "(meth)acrylic" is used to include both "methacrylic" and "acrylic". The same can be applied to similar terms such as "(meth)acryloyl" and "(meth)acrylate".

Examples of a structure having the plurality of independent aromatic rings include a biphenyl skeleton, a diphenylmethyl skeleton, a 2,2-diphenylpropane skeleton, a triphenylmethyl skeleton, a diphenyl ether skeleton, a fluorene skeleton, a carbazole skeleton, and a diphenylamine skeleton. In view of improving solubility, obtaining a low-viscous resin composition for stereolithography, and improving toughness of a cured product, a biphenyl skeleton, a diphenylmethyl skeleton, a 2,2-diphenylpropane skeleton, a triphenylmethyl skeleton, a diphenyl ether skeleton, a fluorene skeleton, and a diphenylamine skeleton are preferred, a biphenyl skeleton, a diphenylmethyl skeleton, a 2,2-diphenylpropane skeleton, a triphenylmethyl skeleton, a diphenyl ether skeleton, and a fluorene skeleton are more preferred, and a triphenylmethyl skeleton and a fluorene skeleton are even more preferred. The term "skeleton" may be interchanged with "group".

The plurality of independent aromatic rings of the α,β-unsaturated double bond group-containing compound (A) can have a substituent such as an alkyl group, an alkoxy group, an ester group, an acyl group, an alkylamino group, a silyl group, a nitro group, a nitroso group, or a halogen atom. The number of substituents is not particularly limited, and is preferably 1 to 6, more preferably 1 to 4, even more preferably 1 to 3, particularly preferably 1 or 2. Examples of the alkyl group and an alkyl group of the alkylamino group include linear or branched alkyl groups having 1 to 12 carbon atoms. Specific examples thereof include a methyl group, an ethyl group, an n-propyl group, an isopropyl group, an n-butyl group, an isobutyl group, a sec-butyl group, a 2-methylpropyl group, a tert-butyl group, an n-pentyl group, an isopentyl group, and a neopentyl group. The number of carbon atoms of the alkyl group and an alkyl group of the alkylamino group is preferably 1 to 6, more preferably 1 to 4, even more preferably 1 to 3.

Examples of the α,β-unsaturated double bond group-containing compound (A) include o-phenylphenyl (meth)acrylate, m-phenylphenyl (meth)acrylate, p-phenylphenyl (meth)acrylate, diphenylmethyl (meth)acrylate, 4-(1-methyl-1-phenylethyl) (meth)acrylate, triphenylmethyl (meth)acrylate, o-phenoxyphenyl (meth)acrylate, m-phenoxyphenyl (meth)acrylate, p-phenoxyphenyl (meth)acrylate, 9-(meth)acryloyloxyfluorene, 9-(meth)acryloyloxymethylfluorene, N-(meth)acryloylcarbazole, N-(meth)acryloylmethylcarbazole, and diphenylacrylamide. These may be used alone, or two or more thereof may be used in combination. In view of obtaining a low-viscous resin composition for stereolithography and improving toughness of a cured product, the α,β-unsaturated double bond group-containing compound (A) is preferably o-phenylphenyl (meth)acrylate, m-phenylphenyl (meth)acrylate, p-phenylphenyl (meth)acrylate, diphenylmethyl (meth)acrylate, 4-(1-methyl-1-phenylethyl) (meth)acrylate, triphenylmethyl (meth)acrylate, 9-(meth)acryloyloxyfluorene, and 9-(meth)acryloyloxymethylfluorene, more preferably p-phenylphenyl (meth)acrylate, diphenylmethyl (meth)acrylate, triphenylmethyl (meth)acrylate, 9-(meth)acryloyloxyfluorene, and 9-(meth)acryloyloxymethylfluorene, even more preferably triphenylmethyl (meth)acrylate, 9-(meth)acryloyloxyfluorene, and 9-(meth)acryloyloxymethylfluorene.

The content of the α,β-unsaturated double bond group-containing compound (A) of the resin composition for stereolithography of the present invention is preferably 1.0 to 80 mass % in the total amount of the α,β-unsaturated double bond group-containing compound (A), the α,β-unsaturated double bond group-containing compound (B), a urethanized (meth)acrylic compound (D), and another polymerizable compound (these may be hereinafter collectively referred to as "polymerizable compounds"). In view of improving fabricability and providing a cured product having improved toughness and water resistance, the content of the α,β-unsaturated double bond group-containing compound (A) is more preferably 2.5 to 60 mass %, even more preferably 5 to 40 mass %.

A,B-Unsaturated Double Bond Group-Containing Compound (B) Having a Homopolymer Glass Transition Temperature (Tg) of Less Than 40° C., Having a Ring Structure, and Having a Normal Boiling Point of 250° C. or More The resin composition for stereolithography of the present invention comprises the α,β-unsaturated double bond group-containing compound (B) having a homopolymer glass transition temperature (Tg) of less than 40° C., having a ring structure, and having a normal boiling point of 250° C. or more (hereinafter, also referred to simply as "α,β-unsaturated double bond group-containing compound (B)"). In the resin composition for stereolithography of the present invention, the α,β-unsaturated double bond group-containing compound (B) is used to lower the viscosity of the resin composition for stereolithography, impart desirable fabricability thereto, and impart toughness and water resistance to a cured product.

Having a normal boiling point of 250° C. or more, the α,β-unsaturated double bond group-containing compound (B) of the present invention can further reduce an odor. An unpleasant odor of the resin composition for stereolithography of the present invention is thus less likely to be perceived. The normal boiling point of the α,β-unsaturated double bond group-containing compound (B) is preferably 275° C. or more, more preferably 300° C. or more. The normal boiling point of the α,β-unsaturated double bond group-containing compound (B) is preferably 450° C. or less, more preferably 400° C. or less. As used herein, "normal boiling point" is a measured value by atmospheric distillation. For compounds for which normal boiling points are not observable, a measured value of boiling point at reduced pressure by vacuum distillation is converted into a normal boiling point using a boiling point vs. pressure chart (The Science of Petroleum, Vol. II. p.1281 (1938)).

It is important that a homopolymer of the α,β-unsaturated double bond group-containing compound (B) of the present invention have a glass transition temperature (Tg) of less than 40° C. With a homopolymer glass transition temperature (Tg) of less than 40° C., an adequately flexible structure is introduced, and therefore a three-dimensional object having favorable toughness can be formed. The homopolymer Tg is preferably 35° C. or less.

It is important for the α,β-unsaturated double bond group-containing compound (B) of the present invention to have a ring structure. Since having a ring structure, the α,β-unsaturated double bond group-containing compound (B) has a high affinity for the α,β-unsaturated double bond group-containing compound (A), and therefore the resulting resin composition for stereolithography has a low viscosity and desirable fabricability. Examples of the ring structure include aromatic rings, heterocyclic rings (for example, heterocyclic rings including at least one atom selected from the group consisting of a nitrogen atom, an oxygen atom, and a sulfur atom), and alicyclic ring. The ring structure is preferably an aromatic ring. The number of rings of the α,β-unsaturated double bond group-containing compound (B) is not particularly limited, and is preferably 1 to 5, more preferably 1 to 4, even more preferably 2 or 3.

In view of obtaining a cured product having desirable toughness, the α,β-unsaturated double bond group-containing compound (B) of the present invention is preferably a monofunctional compound, more preferably a monofunctional (meth)acrylic acid ester compound (B)-1, even more preferably a monofunctional (meth)acrylic acid ester compound having an aromatic ring.

Examples of the monofunctional (meth)acrylic acid ester compound (B)-1 include ethoxylated-o-phenylphenol (meth)acrylate, ethoxylated-m-phenylphenol (meth)acrylate, ethoxylated-p-phenylphenol (meth)acrylate, propoxylated-o-phenylphenol (meth)acrylate, propoxylated-m-phenylphenol (meth)acrylate, propoxylated-p-phenylphenol (meth)acrylate, butoxylated-o-phenylphenol (meth)acrylate, butoxylated-m-phenylphenol (meth)acrylate, butoxylated-p-phenylphenol (meth)acrylate, o-phenoxybenzyl (meth)acrylate, m-phenoxybenzyl (meth)acrylate, p-phenoxybenzyl (meth)acrylate, 2-(o-phenoxyphenyl)ethyl (meth)acrylate, 2-(m-phenoxyphenyl)ethyl (meth)acrylate, 2-(p-phenoxyphenyl)ethyl (meth)acrylate, 3-(o-phenoxyphenyl)propyl (meth)acrylate, 3-(m-phenoxyphenyl)propyl (meth)acrylate, 3-(p-phenoxyphenyl)propyl (meth)acrylate, 4-(o-phenoxyphenyl)butyl (meth)acrylate, 4-(m-phenoxyphenyl)butyl (meth)acrylate, 4-(p-phenoxyphenyl)butyl (meth)acrylate, 5-(o-phenoxyphenyl)pentyl (meth)acrylate, 5-(m-phenoxyphenyl)pentyl (meth)acrylate, 5-(p-phenoxyphenyl)pentyl (meth)acrylate, 6-(o-phenoxyphenyl)hexyl (meth)acrylate, 6-(m-phenoxyphenyl)hexyl (meth)acrylate, 6-(p-phenoxyphenyl)hexyl (meth)acrylate, undecyl (meth)acrylate, lauryl (meth)acrylate, tridecyl (meth)acrylate, tetradecyl (meth)acrylate, pentadecyl (meth)acrylate, cetyl (meth)acrylate, palmitoleyl (meth)acrylate, heptadecyl (meth)acrylate, oleyl (meth)acrylate, stearyl (meth)acrylate, isostearyl (meth)acrylate, 4-hydroxybutyl (meth)acrylate, 6-hydroxyhexyl (meth)acrylate, 10-hydroxydecyl (meth)acrylate, glycerol mono(meth)acrylate, and erythritol mono(meth)acrylate. The α,β-unsaturated double bond group-containing compound (B) may be used alone, or two or more thereof may be used in combination. In view of improving the curability of the resin composition for stereolithography and the toughness and water resistance of a cured product, the α,β-unsaturated double bond group-containing compound (B) preferably has an aromatic ring, and is more preferably o-phenoxybenzyl acrylate, m-phenoxybenzyl acrylate, p-phenoxybenzyl acrylate, 2-(o-phenoxyphenyl)ethyl acrylate, 2-(m-phenoxyphenyl)ethyl acrylate, 2-(p-phenoxyphenyl)ethyl acrylate, ethoxylated-o-phenylphenol (meth)acrylate, ethoxylated-m-phenylphenol (meth)acrylate, and ethoxylated-p-phenylphenol (meth)acrylate, even more preferably o-phenoxybenzyl acrylate, m-phenoxybenzyl acrylate, p-phenoxybenzyl acrylate, and ethoxylated-o-phenylphenol (meth)acrylate, particularly preferably o-phenoxybenzyl acrylate, m-phenoxybenzyl acrylate, and ethoxylated-o-phenylphenol (meth)acrylate, most preferably m-phenoxybenzyl acrylate and ethoxylated-o-phenylphenol (meth)acrylate.

The content of the α,β-unsaturated double bond group-containing compound (B) in the resin composition for stereolithography of the present invention is preferably 1 to 95 mass % in the total amount of the polymerizable compounds. In view of improving fabricability and providing a cured product having improved toughness and water resistance, more preferably 5 to 90 mass %, even more preferably 10 to 80 mass %.

Photopolymerization Initiator (C)

The photopolymerization initiator (C) used in the present invention may be selected from common photopolymerization initiators used in industry, preferably from photopolymerization initiators used in dentistry.

Examples of the photopolymerization initiator (C) include (bis)acylphosphine oxides, thioxanthones or quaternary ammonium salts of thioxanthones, ketals, α-diketones, coumarins, anthraquinones, benzoin alkyl ether compounds, α-aminoketone compounds, and germanium compounds. These may be used alone, or two or more thereof may be used in combination.

Preferably, the photopolymerization initiator (C) is at least one selected from the group consisting of (bis)acylphosphine oxides and α-diketones. In this way, a resin composition for stereolithography can be obtained that has desirable photocurability both in the ultraviolet and visible regions, and that shows sufficient photocurability even when the light source is a laser, a halogen lamp, a light emitting diode (LED), or a xenon lamp.

Examples of acylphosphine oxides in the (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di(2,6-dimethylphenyl)phosphonate, sodium salts of 2,4,6-trimethylbenzoylphenylphosphine oxide, potassium salts of 2,4,6-trimethylbenzoylphenylphosphine oxide, and ammonium salts of 2,4,6-trimethylbenzoyldiphenylphosphine oxide. Examples of bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis(2,5,6-trimethylbenzoyl)-2,4,4-trimethylpentylphosphine oxide. Other examples include the compounds mentioned in JP 2000-159621 A.

Among these (bis)acylphosphine oxides, particularly preferred as photopolymerization initiator (C) are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and sodium salts of 2,4,6-trimethylbenzoylphenylphosphine oxide.

Examples of the α-diketones include diacetyl, benzyl, camphorquinone, 2,3-pentadione, 2,3-octadione, 9,10-phenanthrenequinone, 4,4'-oxybenzyl, and acenaphthenequinone. Camphorquinone is particularly preferred when the light source used is a visible-light source. Examples of the germanium compound include monoacyl germanium compounds such as benzoyltrimethylgermanium (IV); and diacyl germanium compounds such as dibenzoyldiethylgermanium and bis(4-methoxybenzoyl)-diethylgermanium.

The content of the photopolymerization initiator (C) in the resin composition for stereolithography of the present invention is not particularly limited as long as the present invention can exhibit its effects. However, in view of curability, toughness, water resistance, and other properties of the resulting resin composition for stereolithography, the content of the photopolymerization initiator (C) is preferably 0.01 to 20 parts by mass with respect to total 100 parts by mass of the polymerizable compounds. If the content of the photopolymerization initiator (C) is less than 0.01 parts by mass, polymerization may not sufficiently proceed, resulting in a failure to obtain a three-dimensional object. The content of the photopolymerization initiator (C) is more preferably 0.05 parts by mass or more, even more preferably 0.1 parts by mass or more with respect to total 100 parts by mass of the polymerizable compounds. If the content of the photopolymerization initiator (C) is more than 20 parts by mass and the photopolymerization initiator itself has a low solubility, the photopolymerization initiator (C) may precipitate out of the resin composition for stereolithography. The content of the photopolymerization initiator (C) is more preferably 15 parts by mass or less, even more preferably 10 parts by mass or less, particularly preferably 5.0 parts by mass with respect to total 100 parts by mass of the polymerizable compounds.

Urethanized (Meth)Acrylic Compound (D)

The resin composition for stereolithography of the present invention preferably further comprises a urethanized (meth)acrylic compound (D) excluding those falling under the α,β-unsaturated double bond group-containing compound (B). The urethanized (meth)acrylic compound (D) is used to impart curability to the resin composition for stereolithography of the present invention and to impart toughness to a cured product of the resin composition for stereolithography. The urethanized (meth)acrylic compound (D) may be used alone, or two or more thereof may be used in combination.

The urethanized (meth)acrylic compound (D) can be synthesized with ease through addition reaction of, for example, a polyol having any of later-described polymer skeletons, a compound having an isocyanate group (—NCO), and a (meth)acrylate compound having a hydroxyl group (—OH). Alternatively, the urethanized (meth)acrylic compound (D) can be synthesized with ease through ring-opening addition reaction of a (meth)acrylic compound having a hydroxyl group with a lactone or an alkylene oxide and then addition reaction of the resulting compound having a hydroxyl group at one terminal with a compound having an isocyanate group.

The urethanized (meth)acrylic compound (D) is preferably a (meth)acrylate having, per molecule, a urethane bond and at least one structure (polymer skeleton) selected from the group consisting of a polyester, a polycarbonate, a polyurethane, a polyether, a poly(conjugated diene), and a hydrogenated poly(conjugated diene), more preferably a (meth)acrylate having, per molecule, a urethane bond and at least one polyol moiety selected from the group consisting of a polyester, a polycarbonate, a polyurethane, a polyether, a poly(conjugated diene), and a hydrogenated poly(conjugated diene) each having a structure derived from a C4 to C18 aliphatic diol unit (d) having a branched structure. As to the above structure (polymer skeleton), examples of the polyester include a polymer of a dicarboxylic acid (an aromatic dicarboxylic acid such as phthalic acid or isophthalic acid; or an unsaturated aliphatic dicarboxylic acid such as maleic acid) and a C2 to C18 aliphatic diol, a polymer of a dicarboxylic acid (a saturated aliphatic dicarboxylic acid such as adipic acid or sebacic acid) and a C2 to C18 aliphatic diol, a β-propiolactone polymer, a γ-butyrolactone polymer, a δ-valerolactone polymer, an ε-caprolactone polymer, and copolymers thereof, and preferred are a polymer of a dicarboxylic acid (an aromatic dicarboxylic acid such as phthalic acid or isophthalic acid; or an unsaturated aliphatic dicarboxylic acid such as maleic acid) and a C2 to C12 aliphatic diol and a polymer of a dicarboxylic acid (a saturated aliphatic dicarboxylic acid such as adipic acid or sebacic acid) and a C2 to C12 aliphatic diol. Examples of the polycarbonate include polycarbonates derived from a C2 to C18 aliphatic diol, polycarbonates derived from bisphenol A, and polycarbonates derived from a C2 to C18 aliphatic diol and bisphenol A, and preferred are polycarbonates derived from a C2 to C12 aliphatic diol, polycarbonates derived from bisphenol A, and polycarbonates derived from a C2 to C12 aliphatic diol and bisphenol A. Examples of the polyurethane include a polymer of a C2 to C18 aliphatic diol and a C1 to C18 diisocyanate, and preferred is a polymer of a C2 to C12 aliphatic diol and a C1 to C12 diisocyanate. Examples of the polyether include polyethylene glycol, polypropylene glycol, polybutyleneglycol, and poly(1-methylbutyleneglycol). Examples of the poly(conjugated diene) and the hydrogenated poly(conjugated diene) include 1,4-polybutadiene, 1,2-polybutadiene, polyisoprene, poly(butadiene-isoprene), poly(butadiene-styrene), poly(isoprene-styrene), polyfarnesene, and their hydrogenated products. Among these, the structures of the polyesters are preferred in view of desirable toughness. Moreover, in view of desirable water resistance and toughness, the structures of the polyesters preferably comprise a polyol moiety having a structure derived from a C4 to C18 aliphatic diol unit (d) having a branched structure and an isophthalic acid ester or a sebacic acid ester. In view of desirable water resistance and fabricability, the structures of the polyesters more preferably comprise a polyol moiety having a structure derived from a C4 to C12 aliphatic diol unit (d) having a branched structure and an isophthalic acid ester or a sebacic acid ester, and even more preferably comprise a polyol moiety having a structure derived from a C5 to C12 aliphatic diol unit (d) having a branched structure and an isophthalic acid ester or a sebacic acid ester. A polyol having any of the above polymer skeletons can be used to produce the urethanized (meth)acrylic compound (D).

Examples of the compound having an isocyanate group include hexamethylene diisocyanate (HDI), tolylene diisocyanate (TDI), xylylene diisocyanate (XDI), diphenylmethane diisocyanate (MDI), isophorone diisocyanate (IPDI), trimethylhexamethylene diisocyanate (TMHMDI), tricyclodecane diisocyanate (TCDDI), and adamantane diisocyanate (ADI).

Examples of the (meth)acrylic compound having a hydroxyl group include hydroxy(meth)acrylate compounds such as 2-hydroxyethyl (meth)acrylate, 2-hydroxypropyl (meth)acrylate, 2-hydroxybutyl (meth)acrylate, 6-hydroxyhexyl (meth)acrylate, 10-hydroxydecyl (meth)acrylate, 3-chloro-2-hydroxypropyl (meth)acrylate, 2-hydroxy-3-phenoxypropyl (meth)acrylate, glycerin mono(meth)acrylate, N-hydroxyethyl (meth)acrylamide, N,N-bis(2-hydroxyethyl) (meth)acrylamide, 2-hydroxy-3-acryloyloxypropyl (meth)acrylate, 2,2-bis[4-[3-(meth)acryloyloxy-2-hydroxypropoxy]phenyl]propane, 1,2-bis[3-(meth)acryloyloxy-2-hydroxypropoxy]ethane, pentaerythritol tri(meth)acrylate, and dipentaerythritol tri(meth)acrylate or dipentaerythritol tetra(meth)acrylate; and hydroxy (meth)acrylamide compounds such as N-hydroxyethyl (meth)acrylamide and N,N-bis(2-hydroxyethyl) (meth)acrylamide.

Examples of the C4 to C18 aliphatic diol unit (d) having a branched structure include 2-methyl-1,3-propanediol, 2,2-diethyl-1,3-propanediol, 1,3-butanediol, 2-methyl-1,4-butanediol, neopentyl glycol, 3-methyl-1,5-pentanediol, 2-methyl-1,8-octanediol, 2,7-dimethyl-1,8-octanediol, 2-methyl-1,9-nonanediol, 2,8-dimethyl-1,9-nonanediol, 2-methyl-1,10-decanediol, 2,9-dimethyl-1,10-decanediol, 2-m ethyl-1,11-undecanediol, 2,10-dimethyl-1,11-undecanediol, 2-methyl-1,12-dodecanediol, 2,11-dimethyl-1,12-dodecanediol, 2-m ethyl-1,13-tridecaned iol, 2,12-d imethyl-1,13-tridecanediol, 2-methyl-1,14-tetradecanediol, 2,13-dimethyl-1,14-tetradecanediol, 2-methyl-1,15-pentadecanediol, 2,14-dimethyl-1,15-pentadecanediol, 2-methyl-1,16-hexadecanediol, and 2,15-dimethyl-1,16-hexadecanediol. In view of providing the resin composition for stereolithography having desirable curability and low viscosity, polyols used are preferably C5 to C12 aliphatic diols having a methyl-group side chain, for example, such as 2-methyl-1,4-butanediol, 3-methyl-1,5-pentanediol, 2-methyl-1,8-octanediol, 2,7-dimethyl-1,8-octanediol, 2-methyl-1,9-nonanediol, and 2,8-dimethyl-1,9-nonanediol. The polyols are more preferably 2-methyl-1,4-butanediol, 3-methyl-1,5-pentanediol, 2-methyl-1,8-octanediol, and 2,7-dimethyl-1,8-octanediol, even more preferably 3-methyl-1,5-pentanediol, and 2-methyl-1,8-octanediol.

The addition reaction between the compound having an isocyanate group and the (meth)acrylic compound having a hydroxyl group is not particularly limited, and may be carried out according to known methods.

The urethanized (meth)acrylic compound (D) produced by the reaction is, for example, any combination of the polyol having at least one structure selected from the group consisting of a polyester, a polycarbonate, a polyurethane, a polyether, a poly(conjugated diene), and a hydrogenated poly(conjugated diene); the compound having an isocyanate group; and the (meth)acrylic compound having a hydroxyl group.

In view of viscosity and strength, the urethanized (meth) acrylic compound (D) has a weight-average molecular weight (Mw) of preferably 1,000 to 30,000, more preferably 1,500 to 15,000, even more preferably 2,000 to 9,000, yet even more preferably 2,000 to 8,000, particularly preferably 2,000 to 7,000, most preferably 2,000 to 5,000. As used herein, "weight-average molecular weight (Mw)" means a weight-average molecular weight determined in terms of polystyrene by gel permeation chromatography (GPC).

The content of the urethanized (meth)acrylic compound (D) in the resin composition for stereolithography of the present invention is preferably 1 to 98 mass % in the total amount of the polymerizable compounds. In view of improving fabricability and providing a cured product having improved toughness, including flexibility, and water resistance, the content of urethanized (meth)acrylic compound (D) is more preferably 5 to 90 mass %, even more preferably 10 to 80 mass %.

The resin composition for stereolithography of the present invention may comprise an additional polymerizable compound (hereinafter, also referred to as "additional polymerizable compound") other than the α,β-unsaturated double bond group-containing compound (A) and the α,β-unsaturated double bond group-containing compound (B). The polymerizable compounds may consist essentially of the α,β-unsaturated double bond group-containing compound (A) and the α,β-unsaturated double bond group-containing compound (B). That is, the resin composition for stereolithography of the present invention may be essentially free of the additional polymerizable compound (including the urethanized (meth)acrylic compound (D)). Here, essentially consisting of a component means that the content of an additional polymerizable compound other than the component is less than 10.0 mass %, preferably less than 5.0 mass %, more preferably less than 1.0 mass %, even more preferably less than 0.1 mass %, particularly preferably less than 0.01 mass % in the total amount of the polymerizable compounds contained in the resin composition for stereolithography. In another suitable embodiment, in the resin composition for stereolithography of the present invention, the polymerizable compounds may consist essentially of the α,β-unsaturated double bond group-containing compound (A), the α,β-unsaturated double bond group-containing compound (B), and the urethanized (meth)acrylic compound (D). That is, the resin composition for stereolithography of the present invention may be essentially free of the additional polymerizable compound (excluding the urethanized (meth)acrylic compound (D)). Examples of the additional polymerizable compound (excluding the urethanized (meth)acrylic compound (D)) include polyfunctional (meth)acrylic acid ester compounds having two or more polymerizable groups, polyfunctional (meth)acrylamide compounds, and monofunctional (meth)acrylamide compounds. Examples of the polyfunctional (meth)acrylic acid ester compounds include aromatic bifunctional (meth)acrylic acid ester compounds, aliphatic bifunctional (meth)acrylic acid ester compounds, and tri- and higher-functional (meth)acrylic acid ester compounds.

The resin composition for stereolithography of the present invention is not particularly limited as long as it comprises the α,β-unsaturated double bond group-containing compound (A), the α,β-unsaturated double bond group-containing compound (B), and the photopolymerization initiator (C). The resin composition for stereolithography of the present invention can be produced according to a known method.

The resin composition for stereolithography of the present invention may contain a polymerization accelerator to improve photocurability, provided that addition of a polymerization accelerator is not against the intent and purpose of the present invention. Examples of the polymerization accelerator include amine compounds containing an aromatic amine, such as ethyl 4-(N,N-dimethylamino)benzoate, methyl 4-(N,N-dimethylamino)benzoate, n-butoxyethyl 4-(N,N-dimethylamino)benzoate, 2-(methacryloyloxy)ethyl 4-(N,N-dimethylamino)benzoate, 4-(N,N-dimethylamino) benzophenone, and butyl 4-(N,N-dimethylamino)benzoate. In view of imparting desirable curability to the resin composition for stereolithography, preferred is at least one selected from the group consisting of ethyl 4-(N,N-dimethylamino)benzoate, n-butoxyethyl 4-(N,N-dimethylamino) benzoate, and 4-(N,N-dimethylamino)benzophenone.

The resin composition for stereolithography of the present invention may further comprise a filler mixed therein to adjust paste properties or to alter the surface properties or strength of a cured product of the resin composition for stereolithography. Examples of the filler include organic fillers, inorganic fillers, and organic-inorganic composite fillers. The filler may be used alone, or two or more thereof may be used in combination.

Examples of the organic fillers include polymethyl methacrylate, polyethyl methacrylate, methyl methacrylate-ethyl methacrylate copolymer, crosslinked polymethyl methacrylate, crosslinked polyethyl methacrylate, polyesters, polyamides, polycarbonates, polyphenylene ethers, polyoxymethylene, polyvinyl chloride, polystyrene, polyethylene, polypropylene, chloroprene rubber, nitrile rubber, ethylenevinyl acetate copolymer, styrene-butadiene copolymer, acrylonitrile-styrene copolymer, and acrylonitrile-styrene-butadiene copolymer. These may be used alone, or two or more thereof may be used in combination. The organic filler is not limited to a particular shape, and may be appropriately selected from organic fillers of different particle diameters. In view of handling properties, mechanical strength, and other properties of the resulting resin composition for stereolithography, the average particle diameter of the organic filler is preferably 0.001 to 50 μm, more preferably 0.001 to 10 μm, even more preferably 0.001 to 1.0 μm.

Examples of the materials of the inorganic fillers include quartz, silica, alumina, silica-titania, silica-titania-barium oxide, silica-zirconia, silica-alumina, lanthanum glass, borosilicate glass, soda glass, barium glass, strontium glass, glass-ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone, or two or more thereof may be used in combination. The inorganic filler is not limited to a particular shape, and may be appropriately selected from inorganic fillers of different shapes, such as irregularly shaped fillers, and spherical fillers. In view of ease of handling properties, mechanical strength, and other properties of the resulting resin composition for stereolithography, the average particle diameter of the inorganic filler is preferably 0.001 to 50 μm, more preferably 0.001 to 10 μm, even more preferably 0.001 to 1.0 μm.

In order to adjust the flowability of the resin composition for stereolithography, the inorganic filler may be used after an optional surface treatment with a known surface treatment agent such as a silane coupling agent. Examples of the surface treatment agent include vinyltrimethoxysilane, vinyltriethoxysilane, vinyltrichlorosilane, vinyltri(β-methoxyethoxy)silane, γ-methacryloyloxypropyltrimethoxysilane, 8-methacryloyloxyoctyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler used in the present invention is a filler prepared by pulverizing a product of polymerization of a paste-like material prepared by adding a monomer component to the above inorganic filler. As the organic-inorganic composite filler, for example, a TMPT filler (a polymerized and pulverized mixture of trimethylolpropanetrimethacrylate and a silica filler) can be used. The organic-inorganic composite filler is not limited to a particular shape, and may be appropriately selected from organic-inorganic composite fillers of different particle diameters. In view of handling properties, mechanical strength, and other properties of the resulting resin composition for stereolithography, the average particle diameter of the organic-inorganic filler is preferably 0.001 to 50 μm, more preferably 0.001 to 10 μm, even more preferably 0.001 to 1.0 μm.

In the present specification, the average particle diameter of the filler is an average primary particle diameter, and can be determined by a laser diffraction scattering method or by electron microscope observation of the particles. Specifically, the laser diffraction scattering method is convenient for particle diameter measurement on particles with a diameter of 0.1 µm or more, and electron microscope observation is convenient for particle diameter measurement on ultrafine particles with a diameter of less than 0.1 µm. The particle diameter of 0.1 µm is a value determined by the laser diffraction scattering method.

To be specific about the laser diffraction scattering method, for example, the average particle diameter can be measured using a 0.2% aqueous solution of sodium hexametaphosphate as a dispersion medium by means of a laser diffraction particle size distribution analyzer (SALD-2300 manufactured by Shimadzu Corporation).

As a specific example of electron microscopy, particles may be photographed with an electron microscope (Model S-4000, manufactured by Hitachi, Ltd.), and the diameters of particles (at least 200 particles) observed in a unit field of the micrograph may be measured using image-analyzing particle-size-distribution measurement software (Macview, manufactured by Mountech Co., Ltd.). Here, the particle diameters are each determined as an arithmetic mean value of the maximum and minimum lengths of each particle, and the average primary particle diameter is calculated from the number of particles and their particle diameters.

The resin composition for stereolithography of the present invention may comprise a polymer to alter properties such as flexibility and flowability, provided that addition of a polymer is not against the intent and purpose of the present invention. Examples of polymers that may be added in the present invention include natural rubber, synthetic polyisoprene rubber, liquid polyisoprene rubber, hydrogenated products of these, polybutadiene rubber, liquid polybutadiene rubber, hydrogenated products of these, styrene-butadiene rubber, chloroprene rubber, ethylene-propylene rubber, acryl rubber, isoprene-isobutylene rubber, acrylonitrile-butadiene rubber, and styrene elastomers. Specific examples of other polymers that may be added in the present invention include a polystyrene-polyisoprene-polystyrene block copolymer, a polystyrene-polybutadiene-polystyrene block copolymer, a poly($\alpha$-methylstyrene)-polybutadiene-poly($\alpha$-methylstyrene) block copolymer, a poly(p-methylstyrene)-polybutadiene-poly(p-methylstyrene) block copolymer, and hydrogenated products of these.

The resin composition for stereolithography of the present invention may optionally comprise a softener. Examples of the softener include petroleum-base softeners such as paraffinic, naphthenic, and aromatic process oils, and vegetable oil-base softeners such as paraffin, peanut oil, and rosin. These softeners may be used alone, or two or more thereof may be used in combination. The softener content is not particularly limited, provided that it is not against the intent and purpose of the present invention. Typically, the softener content is at most 200 parts by mass, preferably at most 100 parts by mass with respect to total 100 parts by mass of the polymerizable compounds.

The resin composition for stereolithography of the present invention may contain a chemical polymerization initiator to improve curability, provided that it is not against the intent and purpose of the present invention. Preferred as chemical polymerization initiators are organic peroxides and azo compounds. The organic peroxides and azo compounds used as chemical polymerization initiators are not particularly limited, and may be known compounds. Typical examples of organic peroxides include ketone peroxide, hydroperoxides, diacyl peroxides, dialkyl peroxides, peroxyketals, peroxyesters, and peroxydicarbonates. The chemical polymerization initiator may be used alone, or two or more thereof may be used in combination.

The resin composition for stereolithography of the present invention may comprise a known stabilizer, in order to inhibit deterioration, or to adjust photocurability. Examples of such stabilizers include polymerization inhibitors, ultraviolet absorbers, and antioxidants. The stabilizer may be used alone, or two or more thereof may be used in combination.

Examples of the polymerization inhibitors include hydroquinone, hydroquinone monomethyl ether, dibutylhydroquinone, dibutylhydroquinone monomethyl ether, 4-t-butyl catechol, 2-t-butyl-4,6-dimethylphenol, 2,6-di-t-butylphenol, and 3,5-di-t-butyl-4-hydroxytoluene. The content of polymerization inhibitor is preferably 0.001 to 5.0 parts by mass with respect to total 100 parts by mass of the polymerizable compounds.

The resin composition for stereolithography of the present invention may comprise a known additive, in order to adjust shades or paste properties. Examples of such additives include pigments, dyes, organic solvents, and thickeners. The additive may be used alone, or two or more thereof may be used in combination.

The resin composition for stereolithography of the present invention enables easy stereolithographical fabrication of an object (particularly by bottom-up vat stereolithography), and can produce an object having desirable toughness and desirable water resistance. The resin composition for stereolithography of the present invention can also be used for stereolithographic fabrication by an inkjet method. The resin composition for stereolithography of the present invention and a cured product thereof can therefore be used in applications where such advantages can be exploited (for example, intraoral use), and can be used as a dental material or a sleep disorder treatment material. As a dental material, an optimal application is dental treatment using, particularly, dental mouthpieces (such as dental splints, aligners for correction of teeth alignment, and retainers) and denture base materials. Aside from such dental treatment applications using dental mouthpieces and denture base materials, the resin composition for stereolithography of the present invention is also suitable for mouthguards used for protection against external forces in sport activities. Preferably, the resin composition for stereolithography of the present invention is used as a resin composition for bottom-up vat stereolithography because its advantages including toughness, water resistance, and fabricability can be more effectively exploited in such an application. As a sleep disorder treatment material, an optimal application is, particularly, appliances for treatment of sleep apnea. A cured product of the resin composition for stereolithography of the present invention may have a shape that depends on intended use. In the resin composition for stereolithography of the present invention, the type and content of each component (the $\alpha,\beta$-unsaturated double bond group-containing compound (A), the $\alpha,\beta$-unsaturated double bond group-containing compound (B), the photopolymerization initiator (C), the urethanized (meth)acrylic compound (D), and other components such as the polymerization accelerator, the filler, the polymer, the softener, the stabilizer, and the additive) may be optionally adjusted according to use (for example, as a dental mouthpiece or a denture base material).

The resin composition for stereolithography of the present invention can be used in a wide variety of applications by taking advantage of its properties, specifically, the superior shape accuracy due to the low rate of volume shrinkage upon curing with light, and the ability to produce cured products of desirable properties, for example, three-dimensional objects having desirable toughness and water resistance. For example, the resin composition for stereolithography of the present invention can be used for production of a three-dimensional object by stereolithographic modeling; dental materials; production of various molded articles, for example, a film-shaped object or a molding, produced by a technique such as flow casting or casting; and a die for coating or vacuum molding, and is particularly optimal for a dental material.

The resin composition for stereolithography of the present invention is particularly suited for stereolithographic modeling. In stereolithographic modeling applications, the resin composition for stereolithography of the present invention enables smooth production of a three-dimensional object having desirable toughness and water resistance while ensuring superior shape accuracy with a maintained low rate of volume shrinkage at the time of curing with light.

Another embodiment of the present invention is a method for producing a three-dimensional object by stereolithographic modeling using any of the resin compositions for stereolithography described above.

In stereolithography (particularly, bottom-up vat stereolithography) using the resin composition for stereolithography of the present invention, any known bottom-up stereolithographic modeling method and device may be used (for example, a stereolithography device such as the Digital-Wax® 020D manufactured by DWS). A stereolithographic modeling method and device are not particularly limited, and the resin composition for stereolithography of the present invention is particularly suited for a bottom-up stereolithography apparatus (bottom-up vat stereolithography device) in view of the viscosity of the resin composition for stereolithography. In the present invention, the light energy used to cure the resin is preferably an active energy beam. As used herein, "active energy beam" means an energy ray capable of curing the resin composition for stereolithography, and includes, for example, ultraviolet light, an electron beam, X-rays, radiant rays, and high-frequency waves. For example, the active energy beam may be ultraviolet light of 300 to 420 nm wavelengths. The light source of active energy beam may be, for example, a laser such as an Ar laser or a He—Cd laser; or a lighting such as a halogen lamp, a xenon lamp, a metal halide lamp, an LED, a mercury lamp, and a fluorescent lamp. Lasers are particularly preferred. When the light source is a laser, the fabrication time can be reduced by increasing the energy level, and a three-dimensional object of high shape accuracy can be obtained by taking advantage of the desirable convergence of a laser beam.

Stereolithographic modeling using the resin composition for stereolithography of the present invention may use any known method and any known stereolithography system, and the method and device are not particularly limited, as noted above. However, a typical example of a stereolithographic modeling method preferred for use in the present invention is a method that produces a three-dimensional object of the desired shape through a repeated procedure that includes a step of forming a cured layer by selectively applying an active energy beam to the resin composition for stereolithography to obtain a cured layer having a desired pattern, and a step of continuously forming another cured layer thereon by similarly applying an active energy beam to a newly supplied, uncured liquid resin composition for stereolithography. The resulting three-dimensional object may be used as it is, or may be used after improving mechanical strength, shape stability, or other properties by, for example, post-curing the product under applied light or heat.

A cured product of the resin composition for stereolithography of the present invention has a flexural modulus in a range of preferably 0.3 to 3.0 GPa, more preferably 0.5 to 2.5 GPa, even more preferably 0.8 to 2.0 GPa. With a flexural modulus of 2.0 GPa or less, a cured product can have softness, which makes the cured product, for example, a dental mouthpiece, more comfortable to wear by allowing it to more easily conform to the teeth. The cured product also becomes less likely to come off during sleep such as in sleep bruxism. A cured product of the resin composition for stereolithography of the present invention has a flexural strength of preferably 30 MPa or more, more preferably 40 MPa or more, even more preferably 50 MPa or more.

A three-dimensional object obtained by stereolithographic modeling is not limited to a particular structure, shape, or size, and these may be decided according to use. Typical examples of areas to which the stereolithographic modeling of the present invention is applicable include production of various models and molds, including, for example, models for assessing external designs in a designing process; models for checking functions of components and parts; resin molds for making molds; base models for making dies; and direct molds for prototype dies. More specifically, the stereolithography of the present invention is applicable to, for example, production of models or work models for precision components and parts, electrical and electronic components, furniture, architectural structures, automobile parts, various containers and vessels, castings, dies, and base molds.

EXAMPLES

The following describes the present invention in greater detail by way of Examples. It should be noted, however, that the present invention is in no way limited by the following Examples, and various changes may be made by a person with ordinary skill in the art within the technical idea of the present invention.

Components used for resin compositions for stereolithography according to Examples and Comparative Examples are listed below with the abbreviations.

A,B-Unsaturated Double Bond Group-Containing Compound (A)

AFL: 9-Acryloyloxyfluorene (manufactured by Chemsigma International Co., Ltd.; white solids; homopolymer Tg: 100° C. or more)

TPMMA: Triphenylmethyl methacrylate (manufactured by Carbon Scientific; white solids; homopolymer Tg: 100° C. or more)

A,B-Unsaturated Double Bond Group-Containing Compound (B)

Monofunctional (Meth)Acrylic Acid Ester Compound (B)-1

EPPA: Ethoxylated-o-phenylphenol acrylate (A-LEN-10 manufactured by SHIN-NAKAMURA CHEMICAL Co., Ltd.; homopolymer Tg: 33° C.; atmospheric equivalent boiling point: 300° C. or more)

POBA: m-Phenoxybenzyl methacrylate (manufactured by Kyoeisha Chemical Co., Ltd.; colorless transparent liquid; homopolymer Tg: 35° C.; atmospheric equivalent boiling point: 300° C. or more)

Urethanized (Meth)Acrylic Compound (D)

Urethanized (meth)acrylic compounds (D)-1 and (D)-2 produced as described in Synthesis Examples 1 and 2 were used.

Photopolymerization Initiator (C)

TPO: 2,4,6-Trimethylbenzoyl diphenylphosphine oxide

BAPO: Bis(2,4,6-trimethylbenzoyl)phenylphosphine oxide

Polymerization Inhibitor

BHT: 3,5-di-t-Butyl-4-hydroxytoluene

Synthesis Example 1

Production of Urethanized (Meth)Acrylic Compound (D)-1
(1) First, 250 g of isophorone diisocyanate and 0.15 g of di-n-butyltin dilaurate were added into a 5 L four-neck flask equipped with a stirrer, a thermostat, a thermometer, and a condenser, and the mixture was heated to 70° C. while being stirred.
(2) Separately, 2,500 g of a polyester polyol (Kuraray Polyol® P-2030 manufactured by Kuraray Co., Ltd.; a polyol of isophthalic acid and 3-methyl-1,5-pentanediol; a weight-average molecular weight (Mw) of 2,000) was added into a dropping funnel equipped with a side tube, and the solution in the dropping funnel was dropped into the flask of (1). Here, the solution was dropped at a constant rate over a time period of 4 hours with the temperature inside the flask held at 65 to 75° C. while stirring the solution in the flask of (1). After dropping, the mixture was stirred at the same temperature for 2 hours to allow for reaction.
(3) Thereafter, a homogenous solution prepared by adding 150 g of 2-hydroxyethyl acrylate and 0.4 g of hydroquinone monomethyl ether into a different dropping funnel was dropped at a constant rate over a time period of 2 hours with the temperature inside the flask held at 55 to 65° C., and a reaction was allowed for 4 hours at the maintained solution temperature of 70 to 80° C. in the flask to obtain a urethanized (meth)acrylic compound (D)-1. By GPC analysis, the weight-average molecular weight (Mw) of urethanized (meth)acrylic compound (D)-1 was found to be 2,700.

Synthesis Example 2

Production of Urethanized (Meth)Acrylic Compound (D)-2
(1) First, 250 g of isophorone diisocyanate and 0.15 g of di-n-butyltin dilaurate were added into a 5 L four-neck flask equipped with a stirrer, a thermostat, a thermometer, and a condenser, and the mixture was heated to 70° C. while being stirred.
(2) Separately, 2,500 g of a polyester polyol (Kuraray Polyol® P-2050 manufactured by Kuraray Co., Ltd.; a polyol of sebacic acid and 3-methyl-1,5-pentanediol; a weight-average molecular weight (Mw) of 2,000) was added into a dropping funnel equipped with a side tube, and the solution in the dropping funnel was dropped into the flask of (1). Here, the solution was dropped at a constant rate over a time period of 4 hours with the temperature inside the flask held at 65 to 75° C. while stirring the solution in the flask of (1). After dropping, the mixture was stirred at the same temperature for 2 hours to allow for reaction.
(3) Thereafter, a homogenous solution prepared by adding 150 g of 2-hydroxyethyl acrylate and 0.4 g of hydroquinone monomethyl ether into a different dropping funnel was dropped at a constant rate over a time period of 2 hours with the temperature inside the flask held at 55 to 65° C., and a reaction was allowed for 4 hours at the maintained solution temperature of 70 to 80° C. in the flask to obtain a urethanized (meth)acrylic compound (D)-2. By GPC analysis, the weight-average molecular weight (Mw) of urethanized (meth)acrylic compound (D)-2 was found to be 2,600.

Examples 1 to 6 and Comparative Examples 1 to 7

The components were mixed under ordinary temperature (20° C.±15° C., JIS (Japanese Industrial Standards) Z 8703: 1983) in the amounts shown in Tables 1 and 2 to prepare pastes as resin compositions for stereolithography according to Examples 1 to 6 and Comparative Examples 1 to 7.

Fabricability
The resin compositions for stereolithography according to Examples and Comparative Examples were each fabricated into a specimen measuring 3.3 mm in thickness, 10.0 mm in width, and 64 mm in length (n=5), using a stereolithography device (DigitalWax® 020D, manufactured by DWS). The resin composition was determined as "Satisfactory" when it was fabricable into a sheet of the desired dimensions in all five specimens, and "Unsatisfactory" when the resin composition was not fabricable into a desired three-dimensional object in any of the five specimens. The specimens were used for the following evaluations. Tables 1 and 2 show the evaluation results.

Toughness (Flexural Modulus, Flexural Strength, Displacement of Fracture Point)
A cured product of the resin composition for stereolithography of each Example and Comparative Example was fabricated into a specimen (64.0 mm in length, 10.0 mm in width, 3.3 mm in thickness) as used in the evaluation of fabricability, the specimen having dimensions described in JIS T 6501: 2012 (Acrylic Resin for Denture Base). The specimen was stored in the air for one day and then evaluated in a flexural strength test to obtain an initial value. That is, the flexural strength test was conducted using a universal testing machine (Autograph AG-I, 100 kN, manufactured by Shimadzu Corporation) at a crosshead speed of 5 mm/min (n=5). The flexural strength and flexural modulus of the cured product were found by calculating means from values measured for each specimen. The preferred range of specimen's flexural modulus is 0.3 to 3.0 GPa, more preferably 0.5 to 2.5 GPa, even more preferably 0.8 to 2.0 GPa. The preferred range of flexural strength is 30 MPa or more, more preferably 40 MPa or more, even more preferably 50 MPa or more. As for the displacement of fracture point, the specimen was determined as being desirable when there was no fracture. Flexibility was determined as being desirable (Satisfactory) when the specimen did not have a fracture at the end of testing, or when a fracture occurred with a displacement of 20 mm or more, moderate (Acceptable) when a fracture occurred with a displacement of more than 10 mm and less than 20 mm, and poor (Unsatisfactory) when a fracture occurred with a displacement of 10 mm or less.

Water Resistance
A cured product of the resin composition for stereolithography of each Example and Comparative Example produced in the same manner as for the cured products produced for the measurement of toughness was immersed in 37° C. water for 168 hours, and measured for flexural strength in the same manner as in the flexural strength test above (n=5). Water resistance is desirable when the rate of change (rate of decrease) of flexural strength after 168-hour immersion in 37° C. water is 10% or less relative to the initial flexural strength taken from the result of the flexural strength measurement conducted for evaluation of toughness. Water resistance is more desirable when the rate of change (rate of decrease) is 7% or less. In Tables 1 and 2, the flexural strength after 168-hour immersion in 37° C. water is shown as "flexural strength after immersion".

Rate of change (rate of decrease) of flexural strength (%)=[{initial flexural strength (MPa)−flexural strength (MPa) after 168-hour immersion in 37° C. water}/initial flexural strength (MPa)]×100

Odor
The resin composition for stereolithography of each Example and Comparative Example was evaluated for odor by a group of 10 panelists (n=1). The resin composition was evaluated as "Satisfactory" when fewer than 2 panelists felt an unpleasant odor, "Acceptable" when at least 2 and fewer than 5 panelists felt an unpleasant odor, and "Unsatisfactory" when 5 or more panelists felt an unpleasant odor. The resin compositions are of satisfactory quality when there is no perceivable unpleasant odor.

desirable toughness and water resistance. In particular, the cured products of the resin compositions for stereolithography according to Examples 1 to 6 have more desirable toughness and water resistance than the cured products of

TABLE 1

| Component (parts by mass) | | Example 1 | Example 2 | Example 3 | Example 4 | Example 5 | Example 6 |
|---|---|---|---|---|---|---|---|
| (A) | AFL | 15 | 25 | 35 | 35 | | 30 |
| | TPMMA | | | | | 25 | |
| (B) | EPPA | 10 | 25 | 25 | 20 | 25 | 20 |
| | POBA | 25 | 10 | 10 | | 10 | 10 |
| (D) | Urethanized (meth)acrylic compound (D)-1 | 50 | 40 | 30 | | 40 | 20 |
| | Urethanized (meth)acrylic compound (D)-2 | | | | 45 | | 20 |
| (C) | TPO | 5 | 5 | 5 | 5 | 5 | 3 |
| | BAPO | | | | | | 0.5 |
| | BHT | 1.0 | 1.0 | 1.0 | 1.0 | 1.0 | 1.0 |
| Fabricability | | Satisfactory | Satisfactory | Satisfactory | Satisfactory | Satisfactory | Satisfactory |
| Toughness | Flexural modulus (GPa) | 1.3 | 1.7 | 1.9 | 1.4 | 1.9 | 1.6 |
| | Flexural strength (MPa) | 54 | 57 | 54 | 48 | 49 | 52 |
| | Displacement of fracture point | Satisfactory | Satisfactory | Satisfactory | Satisfactory | Satisfactory | Satisfactory |
| Water resistance | Flexural strength (MPa) after immersion | 52 | 55 | 52 | 45 | 47 | 51 |
| | Rate of decrease (%) | 3.7 | 3.5 | 3.7 | 6.3 | 4.1 | 1.9 |
| Odor | | Satisfactory | Satisfactory | Satisfactory | Satisfactory | Satisfactory | Satisfactory |

TABLE 2

| Component (parts by mass) | | Comparative Example 1 | 2 | 3 | 4 | 5 | 6 | 7 |
|---|---|---|---|---|---|---|---|---|
| (B) | EPPA | 50 | | | | | 25 | 25 |
| | POBA | 10 | | | | | 10 | 10 |
| (D) | Urethanized (meth)acrylic compound (D)-1 | 40 | 30 | 70 | 30 | 70 | 40 | 40 |
| | DCPA | | 70 | 30 | | | | |
| | ACMO | | | | 70 | 30 | | |
| | AMM | | | | | | 25 | |
| | IBA | | | | | | | 25 |
| (C) | TPO | 5 | 5 | 5 | 5 | 5 | 5 | 5 |
| | BAPO | | | | | | | |
| | BHT | 1.0 | 1.0 | 1.0 | 1.0 | 1.0 | 1.0 | 1.0 |
| Fabricability | | Satisfactory | Unsatisfactory | Satisfactory | Satisfactory | Satisfactory | Undissolved | Satisfactory |
| Toughness | Flexural modulus (GPa) | 0.2 | | 0.2 | 3.2 | 1.6 | | 1.2 |
| | Flexural strength (MPa) | 28 | | 26 | 58 | 55 | | 44 |
| | Displacement of fracture point | Satisfactory | | Unsatisfactory | Unsatisfactory | Acceptable | | Acceptable |
| Water resistance | Flexural strength (MPa) after immersion | 25 | | 18 | 3 | 12 | | 40 |
| | Rate of decrease (%) | 10.7 | | 30.7 | 94.4 | 78.1 | | 9.1 |
| Odor | | Satisfactory | Acceptable | Acceptable | Satisfactory | Satisfactory | Satisfactory | Unsatisfactory |

DCPA: Dicyclopentenyl acrylate (manufactured by Hitachi Chemical Company; homopolymer Tg: 120° C.; atmospheric equivalent boiling point: 252° C.)
ACMO: N-Acryloylmorpholine (manufactured by KJ CHEMICALS CORPORATION; homopolymer Tg: 145° C.; atmospheric equivalent boiling point: 255° C.)
AMM: 9-Anthrylmethyl methacrylate (manufactured by Tokyo Chemical Industry Co., Ltd.; homopolymer Tg: 100° C. or more; atmospheric equivalent boiling point: 300° C. or more)
IBA: Isobornyl acrylate (manufactured by Tokyo Chemical Industry Co., Ltd.; homopolymer Tg: 94 to 97° C.; atmospheric equivalent boiling point: 245° C.)

As shown in Tables 1 and 2, the resin compositions for stereolithography of Examples 1 to 6 have desirable fabricability and a weak odor and the cured products thereof have the resin compositions according to Comparative Examples 3 to 5 not containing the α,β-unsaturated double bond group-containing compounds (A) and (B) of the present invention and the cured products of the resin compositions according to Comparative Examples 1 to 7 not containing the α,β-unsaturated double bond group-containing compound (A) of the present invention. The resin composition for stereolithography according to Comparative Example 2 not containing the α,β-unsaturated double bond group-containing compounds (A) and (B) has such inferior fabricability that a specimen was unable to be fabricated and the properties were unable to be measured. It was impossible to homogeneously dissolve the resin composition of Comparative Example 6 containing a fused-ring compound. The resin composition of Comparative Example 6 also emits an unpleasant odor.

INDUSTRIAL APPLICABILITY

The resin composition for stereolithography of the present invention enables easy fabrication of an object, emits a weak odor, and can be made into an object having desirable toughness and water resistance when used for stereolithographical fabrication. A cured product thereof is therefore suited for dental materials (particularly dental mouthpieces and denture base materials) and sleep disorder treatment materials (particularly appliances for treatment of sleep apnea).

The invention claimed is:

1. A dental material resin, comprising a cured product of a resin composition, comprising:
   a monofunctional (meth)acrylic acid ester compound (A)-1 having a homopolymer glass transition temperature (Tg) of 40° C. or more, comprising a plurality of independent aromatic rings, and comprising no urethane bond;
   an α,β-unsaturated double bond group-comprising compound (B) having a homopolymer glass transition temperature (Tg) of less than 40° C., having a ring structure, and having a normal boiling point of 250° C. or more; and
   a photopolymerization initiator (C).

2. The dental material of claim 1, wherein the plurality of independent aromatic rings are each a biphenyl skeleton, a diphenylmethyl skeleton, a 2,2-diphenylpropane skeleton, a triphenylmethyl skeleton, a diphenyl ether skeleton, a fluorene skeleton, a carbazole skeleton, or a diphenylamine skeleton.

3. The dental material of claim 1, wherein the plurality of independent aromatic rings are each a biphenyl skeleton, a diphenylmethyl skeleton, a 2,2-diphenylpropane skeleton, a triphenylmethyl skeleton, a diphenyl ether skeleton, a fluorene skeleton, or a diphenylamine skeleton.

4. The dental material of claim 1, wherein the plurality of independent aromatic rings are each a triphenylmethyl skeleton or a fluorene skeleton.

5. The dental material of claim 1, wherein the monofunctional (meth)acrylic acid ester compound (A)-1 is at least one selected from the group consisting of triphenylmethyl (meth)acrylate, 9-(meth)acryloyloxyfluorene, and 9-(meth)acryloyloxymethylfluorene.

6. The dental material of claim 1, wherein the α,β-unsaturated double bond group-comprising compound (B) is a monofunctional compound.

7. The dental material of claim 1, wherein the α,β-unsaturated double bond group-comprising compound (B) is a monofunctional (meth)acrylic acid ester compound (B)-1.

8. The dental material of claim 1, wherein the ring structure of the α,β-unsaturated double bond group-comprising compound (B) is an aromatic ring.

9. The dental material of claim 1, wherein the α,β-unsaturated double bond group-comprising compound (B) is at least one selected from the group consisting of o-phenoxybenzyl acrylate, m-phenoxybenzyl acrylate, p-phenoxybenzyl acrylate, 2-(o-phenoxyphenyl)ethyl acrylate, 2-(m-phenoxyphenyl)ethyl acrylate, 2-(p-phenoxyphenyl)ethyl acrylate, ethoxylated-o-phenylphenol (meth)acrylate, ethoxylated-m-phenylphenol (meth)acrylate, and ethoxylated-p-phenylphenol (meth)acrylate.

10. The dental material of claim 1, further comprising:
    a urethanized (meth)acrylic compound (D) excluding those falling under the α,β-unsaturated double bond group-comprising compound (B).

11. The dental material of claim 10, wherein the urethanized (meth)acrylic compound (D) is a (meth)acrylate having, per molecule, a urethane bond and at least one structure selected from the group consisting of a polyester, a polycarbonate, a polyurethane, a polyether, a poly (conjugated diene), and a hydrogenated poly(conjugated diene).

12. The dental material of claim 11, wherein the urethanized (meth)acrylic compound (D) is a (meth)acrylate having, per molecule, at least one polyol moiety selected from the group consisting of a polyester, a polycarbonate, a polyurethane, a polyether, a poly(conjugated diene), and a hydrogenated poly(conjugated diene) each having a structure derived from a C4 to C18 aliphatic diol unit (d) having a branched structure.

13. A sleep disorder mouthpiece comprising a cured product of a resin composition comprising:
    a monofunctional (meth)acrylic acid ester compound (A)-1 having a homopolymer glass transition temperature (Tg) of 40° C. or more, comprising a plurality of independent aromatic rings, and comprising no urethane bond;
    an α,β-unsaturated double bond group-comprising compound (B) having a homopolymer glass transition temperature (Tg) of less than 40° C., having a ring structure, and having a normal boiling point of 250° C. or more; and
    a photopolymerization initiator (C).

14. The sleep disorder mouthpiece of claim 13, wherein the plurality of independent aromatic rings are each a biphenyl skeleton, a diphenylmethyl skeleton, a 2,2-diphenylpropane skeleton, a triphenylmethyl skeleton, a diphenyl ether skeleton, a fluorene skeleton, a carbazole skeleton, or a diphenylamine skeleton.

15. The sleep disorder mouthpiece of claim 13, wherein the plurality of independent aromatic rings are each a biphenyl skeleton, a diphenylmethyl skeleton, a 2,2-diphenylpropane skeleton, a triphenylmethyl skeleton, a diphenyl ether skeleton, a fluorene skeleton, or a diphenylamine skeleton.

16. The sleep disorder mouthpiece of claim 13, wherein the plurality of independent aromatic rings are each a triphenylmethyl skeleton or a fluorene skeleton.

17. The sleep disorder mouthpiece of claim 13, wherein the monofunctional (meth)acrylic acid ester compound (A)-1 is at least one selected from the group consisting of triphenylmethyl (meth)acrylate, 9-(meth)acryloyloxyfluorene, and 9-(meth)acryloyloxymethylfluorene.

18. The sleep disorder mouthpiece of claim 13, wherein the α,β-unsaturated double bond group-comprising compound (B) is a monofunctional compound.

19. The sleep disorder mouthpiece of claim 13, wherein the 60 ,β-unsaturated double bond group-comprising compound (B) is a monofunctional (meth)acrylic acid ester compound (B)-1.

20. The sleep disorder mouthpiece of claim 13, wherein the ring structure of the α,β-unsaturated double bond group-comprising compound (B) is an aromatic ring.

21. The sleep disorder mouthpiece of claim 13, wherein the α,β-unsaturated double bond group-comprising compound (B) is at least one selected from the group consisting of o-phenoxybenzyl acrylate, m-phenoxybenzyl acrylate, p-phenoxybenzyl acrylate, 2-(o-phenoxyphenyl)ethyl acrylate, 2-(m-phenoxyphenyl)ethyl acrylate, 2-(p-phenoxyphenyl)ethyl acrylate, ethoxylated-o-phenylphenol (meth)acrylate, ethoxylated-m-phenylphenol (meth)acrylate, and ethoxylated-p-phenylphenol (meth)acrylate.

22. The sleep disorder mouthpiece of claim 13, further comprising:
    a urethanized (meth)acrylic compound (D) excluding those falling under the α,β-unsaturated double bond group-comprising compound (B).

23. The sleep disorder mouthpiece of claim 22, wherein the urethanized (meth)acrylic compound (D) is a (meth)acrylate having, per molecule, a urethane bond and at least one structure selected from the group consisting of a polyester, a polycarbonate, a polyurethane, a polyether, a poly(conjugated diene), and a hydrogenated poly(conjugated diene).

24. The sleep disorder mouthpiece of claim 23, wherein the urethanized (meth)acrylic compound (D) is a (meth)acrylate having, per molecule, at least one polyol moiety selected from the group consisting of a polyester, a polycarbonate, a polyurethane, a polyether, a poly(conjugated diene), and a hydrogenated poly(conjugated diene) each having a structure derived from a C4 to C18 aliphatic diol unit (d) having a branched structure.

\* \* \* \* \*